(12) United States Patent
Knebel et al.

(10) Patent No.: US 8,039,664 B2
(45) Date of Patent: *Oct. 18, 2011

(54) METHOD FOR PRODUCING BUTANEDIOL DIMETHACRYLATES

(75) Inventors: Joachim Knebel, Alsbach-Haehnlein (DE); Thorben Schuetz, Seeheim-Jugenheim (DE); Harald Trauthwein, Buerstadt (DE); Thomas Kehr, Muehltal (DE); Guenther Lauster, Worms (DE); Guido Protzmann, Bensheim (DE); Gerhard Koelbl, Gernsheim (DE); Guenter Westhaeuser, Guntersblum (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/667,822

(22) PCT Filed: May 8, 2008

(86) PCT No.: PCT/EP2008/055666
§ 371 (c)(1),
(2), (4) Date: Jan. 28, 2010

(87) PCT Pub. No.: WO2009/003743
PCT Pub. Date: Jan. 8, 2009

(65) Prior Publication Data
US 2010/0197955 A1 Aug. 5, 2010

(30) Foreign Application Priority Data
Jul. 5, 2007 (DE) .......................... 10 2007 031 474

(51) Int. Cl.
*C07C 67/02* (2006.01)

(52) U.S. Cl. ..................................................... 560/217
(58) Field of Classification Search .................... None
See application file for complete search history.

(56) References Cited

U.S. PATENT DOCUMENTS 4,672,105 A * 6/1987 Schlosser et al. ............. 560/217
5,362,904 A * 11/1994 Kearns .......................... 560/217

FOREIGN PATENT DOCUMENTS
EP 0 534 666 3/1993

OTHER PUBLICATIONS

U.S. Appl. No. 12/667,604, filed Jan. 4, 2010, Schmitt, et al.
U.S. Appl. No. 12/667,538, filed Jan. 4, 2010, Knebel, et al.
U.S. Appl. No. 12/667,599, filed Jan. 4, 2010, Protzmann, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The present invention relates to a process for preparing butanediol dimethacrylates, which comprises the transesterification of butanediol with an ester of methacrylic acid in the presence of catalysts, wherein a combination comprising at least one lithium compound and at least one calcium compound is used as catalyst, at least one of the compounds of lithium and/or of calcium is an oxide, a hydroxide, an alkoxide having from 1 to 4 carbon atoms or a carboxylate having from 1 to 4 carbon atoms and at least part of the reaction is carried out in the presence of an effective amount of water. The process of the invention makes a particularly inexpensive preparation of butanediol dimethacrylates having a very high purity possible.

34 Claims, No Drawings

METHOD FOR PRODUCING BUTANEDIOL DIMETHACRYLATES

The present invention relates to a process for preparing butanediol dimethacrylates.

Butanediol dimethacrylates are widely used as comonomers. Accordingly, a variety of methods of obtaining these compounds are known. To improve the yield and selectivity of the reaction, it is possible to use various catalysts.

For example, the publication DE 28 05 702 describes the preparation of esters of unsaturated carboxylic acids. To catalyze the reactions described, it is possible to use, in particular, compounds containing zirconium and/or calcium. A particularly suitable catalyst is, in particular, zirconium acetylacetonate. The preparation of 1,3-butanediol dimethacrylate is explicitly described. The reactions lead to high yields of about 97%, based on the alcohol used. However, the process has the disadvantage that the catalyst is relatively expensive and can be separated off from the reaction mixture only with great difficulty.

A process for separating off this catalyst is disclosed in DE 199 40 622, but the process is relatively expensive to carry out.

Furthermore, it is possible to use acids or bases for catalyzing the transesterification. Such catalysts are disclosed, for example, in CN 1355161, DE 34 23 443 or EP-A-0 534 666. However, when these catalysts are used, secondary reactions such as the Michael addition which reduces both the purity of the desired dimethacrylate and the yield have to be expected.

In view of the prior art, it was an object of the present invention to provide a process for preparing butanediol dimethacrylates, in which the product can be obtained very inexpensively. Furthermore, the butanediol dimethacrylate obtained should contain only very small amounts of by-products and catalyst residues.

A further object of the invention was to invent a process in which butanediol dimethacrylate can be obtained very selectively.

In addition, it was an object of the present invention to provide a process for preparing butanediol dimethacrylates which can be carried out simply and inexpensively. Here, the product should be obtained in high yields and, viewed overall, with a low energy consumption.

These objects and also further objects which are not explicitly mentioned but can readily be derived or deduced from the relationships discussed here are achieved by a process having all features of Claim 1. Advantageous modifications of the process of the invention are protected in the dependent claims which refer back to Claim 1.

The present invention accordingly provides a process for preparing butanediol dimethacrylates, which comprises the transesterification of butanediol with an ester of methacrylic acid in the presence of catalysts, wherein a combination comprising at least one lithium compound and at least one calcium compound is used as catalyst, at least one of the compounds of lithium and/or of calcium is an oxide, a hydroxide, an alkoxide having from 1 to 4 carbon atoms or a carboxylate having from 1 to 4 carbon atoms and at least part of the reaction is carried out in the presence of an effective amount of water.

This makes it possible to provide, in an unforeseeable way, a process for preparing butanediol dimethacrylates, in which the product is obtained very inexpensively. The product obtained surprisingly contains only very small amounts of by-products and catalyst residues.

Furthermore, the process of the invention makes a particularly selective preparation of butanediol dimethacrylates possible.

In addition, the process of the invention can be carried out simply and inexpensively, and the product can be obtained in high yields and, viewed overall, with a low energy consumption.

According to the invention, at least one butanediol dimethacrylate is prepared. According to the invention, it is possible to prepare 1,3-butanediol dimethacrylate (1,3-butanediyl 2-methylpropenoate), 1,4-butanediol dimethacrylate (1,4-butanediyl 2-methylpropenoate) or a mixture comprising 1,3-butanediol dimethacrylate and 1,4-butanediol dimethacrylate. Both compounds have been known for a long time, with 1,3-butanediol dimethacrylate having the CAS number 1189-08-8 and 1,4-butanediol dimethacrylate having the CAS number 2082-81-7.

The preparation of butanediol dimethacrylate is, according to the invention, carried out using 1,3-butanediol and/or 1,4-butanediol. The compounds are commercially available from, for example, BASF AG or Celanese AG. The CAS number of 1,3-butanediol is 107-88-0, and that of 1,4-butanediol is 110-63-4.

According to the present invention, butanediol is reacted with an ester of methacrylic acid. Particularly suitable methacrylates are formed, in particular, by alcohols having from 1 to 4 carbon atoms. These include, in particular, methanol, ethanol, n-propanol, isopropanol, n-butanol and tert-butanol. Particular preference is given to using, in particular, ethyl methacrylate or methyl methacrylate, with methyl methacrylate being very particularly preferred.

The weight ratio of butanediol to the ester of methacrylic acid is preferably in the range from 1:2 to 1:20, particularly preferably from 1:3 to 1:10 and very particularly preferably in the range from 1:4 to 1:8.

According to the invention, the present transesterification is catalyzed using a combination comprising at least one lithium compound and at least one calcium compound, with at least one of the compounds of lithium and/or of calcium being an oxide, a hydroxide, an alkoxide having from 1 to 4 carbon atoms or a carboxylate having from 1 to 4 carbon atoms. The catalyst preferably comprises at least one lithium compound selected from the group consisting of lithium oxide ($Li_2O$), lithium hydroxide (LiOH), lithium alkoxide having from 1 to 4 carbon atoms, e.g. lithium methoxide ($Li(CH_3O)$), lithium ethoxide ($Li(CH_3CH_2O)$), and/or lithium carboxylate having from 1 to 4 carbon atoms, for example lithium acetate, and at least one calcium compound selected from the group consisting of calcium oxide (CaO), calcium hydroxide ($Ca(OH)_2$), calcium alkoxide having from 1 to 4 carbon atoms, e.g. calcium methoxide ($Ca(CH_3O)_2$), calcium ethoxide ($Ca(CH_3CH_2O)_2$), and/or calcium carboxylate having from 1 to 4 carbon atoms, for example calcium acetate.

The compounds of lithium and/or of calcium can preferably be basic in nature, i.e. dissolution in water results in an increase in the pH.

The catalyst can advantageously contain, for example, lithium hydroxide (LiOH), lithium oxide ($Li_2O$), lithium methoxide ($Ca(CH_3O)_2$) and/or lithium ethoxide ($Li(CH_3CH_2O)$) as lithium compound.

Further catalysts of particular interest are catalysts which comprise calcium oxide (CaO), calcium hydroxide ($Ca(OH)_2$), calcium methoxide ($Ca(CH_3O)_2$) and/or calcium ethoxide ($Ca(CH_3CH_2O)_2$) as calcium compound.

Preference is given to using a mixture comprising lithium hydroxide and calcium oxide or lithium hydroxide and calcium hydroxide as catalyst.

The ratio of the weight of the lithium compound to the weight of the calcium compound can, depending on the reaction conditions, be within a wide range. This ratio can advantageously be, for example, in the range from 20:1 to 1:20, particularly preferably in the range from 1:1 to 1:10.

The amount of catalyst used can be within a wide range. However, processes in which the proportion of catalyst, based on the weight of the butanediol used, is in the range from 0.05 to 8% by weight, preferably in the range from 0.01 to 5% by weight and particularly preferably in the range from 0.1 to 1% by weight, are of particular interest.

According to the invention, the reaction is carried out in the presence of an effective amount of water. The expression "effective amount" means that the amount of water is sufficiently high for an appreciable improvement in the selectivity compared to a reaction under water-free conditions to be achieved. Water is therefore preferably added to the reaction mixture. However, when starting materials having a particularly high water content are used, addition of water can be dispensed with.

In general, the amount of water, based on the weight of the butanediol used, is in the range from 0.005 to 8% by weight, preferably in the range from 0.01 to 4% by weight and particularly preferably in the range from 0.1 to 1% by weight.

According to a particular aspect of the present process, the ratio of the weight of water to the weight of the catalyst can be in the range from 10:1 to 1:10, preferably from 5:1 to 1:5 and particularly preferably in the range from 2:1 to 1:2.

As mentioned above, the catalyst according to the invention comprises at least one lithium compound and at least one calcium compound. Based on the weight of the individual components, the following proportions of water are preferred, without this constituting a restriction. For example, the weight ratio of water to the lithium compound can be in the range from 20:1 to 1:1, preferably from 10:1 to 2:1, and the weight ratio of water to the calcium compound can be in the range from 10:1 to 1:2, particularly preferably from 5:1 to 1:1.75.

According to the invention, at least part of the reaction is carried out in the presence of water. Accordingly, it is not necessary for the abovementioned amounts to be adhered to over the entire course of the transesterification. Rather, these figures relate to the proportion of water at the beginning of the reaction in the case of batch processes. In the case of continuous transesterification reactions, these figures can relate to the starting material mixture added. It has to be taken into account here that part of the water can usually be separated off from the reaction mixture during the course of the reaction, for example by formation of azeotropes together with the alcohols and/or the esters of methacrylic acid used. The proportion of water can therefore decrease during the course of the reaction.

The reaction can be carried out at superatmospheric pressure or subatmospheric pressure. In a particularly advantageous modification of the present invention, the transesterification can be carried out at a pressure in the range from 200 to 2000 mbar, particularly preferably in the range from 500 to 1300 mbar.

The reaction temperature can, in particular as a function of the pressure, likewise be within a wide range. In a preferred embodiment of the present invention, the reaction is preferably carried out at a temperature in the range from 60° C. to 150° C., particularly preferably in the range from 80° C. to 140° C. and very particularly preferably from 90 to 130° C.

Particular advantages can surprisingly be achieved if the temperature at which the reaction occurs is increased during the course of the reaction. In this preferred modification of the process of the invention, the temperature at the beginning of the reaction, in particular to a conversion of 80%, preferably to a conversion of 70%, based on the weight of the butanediol used, can preferably be in the range from 90° C. to 110° C. and that toward the end of the reaction, in particular after a conversion of 80%, preferably after a conversion of 90%, based on the weight of the butanediol used, can be in the range from 115° C. to 130° C.

The transesterification can be carried out either continuously or batchwise. The process of the invention can be carried out in bulk, i.e. without use of a further solvent. If desired, an inert solvent can also be used. Such solvents include, inter alia, petroleum spirit, benzene, toluene, n-hexane, cyclohexane and methyl isobutyl ketone (MIBK), methyl ethyl ketone (MEK).

In a particularly advantageous variant of the transesterification according to the invention, all components such as the butanediol, the methacrylic ester and the catalyst are mixed, after which this reaction mixture is heated to boiling. The alcohol liberated, for example methanol or ethanol, can subsequently be removed from the reaction mixture, if appropriate azeotropically together with methyl methacrylate or ethyl methacrylate.

The reaction times are dependent, inter alia, on the parameters selected, for example pressure and temperature. However, they are generally in the range from 1 to 24 hours, preferably from 2 to 20 hours and very particularly preferably from 6 to 9 hours. In continuous processes, the residence times are generally in the range from 0.5 to 24 hours, preferably from 1 to 12 hours and very particularly preferably from 2 to 3 hours. A person skilled in the art can find further information on the reaction times in the accompanying examples.

The reaction can preferably take place with stirring, with the stirring rate particularly preferably being in the range from 50 to 2000 rpm, very particularly preferably in the range from 100 to 500 rpm.

The pH can be within a wide range. The reaction can advantageously be carried out at a pH in the range from 8 to 14, preferably from 9 to 13.

To prevent undesirable polymerization of the methacrylates, polymerization inhibitors can be used in the reaction. These compounds, for example hydroquinones, hydroquinone ethers such as hydroquinone monomethyl ether or di-tert-butylcatechol, phenothiazine, 4-hydroxy-2,2,6,6-tetramethylpiperidin-1-oxyl, N,N'-diphenyl-p-phenylenediamine, methylene blue or sterically hindered phenols, are well known in the art. These compounds can be used individually or in the form of mixtures and are generally commercially available. The mode of action of the stabilizers is usually that they act as free-radical scavengers for the free radicals occurring in the polymerization. Further details may be found in the relevant specialist literature, in particular Römpp-Lexikon Chemie; editor: J. Falbe, M. Regitz; Stuttgart, N.Y.; 10th Edition (1996); keyword "Antioxidantien" and the references cited here.

Preference is given to using, in particular, phenols as polymerization inhibitor. Particularly surprising advantages can be achieved when using hydroquinone monomethyl ether. Based on the weight of the total reaction mixture, the proportion of inhibitors, either individually or as a mixture, can generally be 0.01-0.5% (wt/wt).

These polymerization inhibitors can be added to the reaction mixture before or at the beginning of the reaction. Furthermore, small proportions of the polymerization inhibitors employed can be introduced during the transesterification. Processes in which part of the polymerization inhibitor is added via the column runback are of particular interest here. This measure makes it possible, in particular, to avoid undesirable polymerization within the distillation column.

Furthermore, oxygen can be used for the inhibition. This can be used, for example, in the form of air, with the amounts introduced advantageously being such that the content in the gas phase above the reaction mixture remains below the explosive limit. Amounts of air in the range from 0.05 to 0.5 l per hour and mole of butanediol are particularly preferred here. In batch processes, this amount can be based on the amount of butanediol originally used. In the case of continuous processes, this amount can be based on the amount of butanediol fed in.

In a particular embodiment of the present invention, a combination of oxygen with at least one phenol, preferably hydroquinone monomethyl ether, can be used for inhibition. It is likewise possible to use inert gas/oxygen mixtures, e.g. nitrogen/oxygen or argon/oxygen mixtures.

In an advantageous embodiment of the present invention, the alcohol liberated from the methacrylate used, for example methanol and/or ethanol, can be separated off by distillation. Here, a mixture containing, for example, methyl methacrylate and methanol can advantageously be separated off. Surprisingly, part of the mixture which has been separated off can advantageously be recirculated to the next batch. In this modification, the proportion which can be recirculated of the mixture which has been separated off can be obtained at the end of the reaction, in particular after a conversion of 80%, preferably after a conversion of 90%, of the butanediol used. For example, the proportion of the recirculated mixture at the beginning of the next batch can be in the range from 40 to 60%, based on the total weight of methacrylic ester to be transesterified.

Batch processes in which methyl methacrylate is added during the transesterification are, inter alia, of particular interest. This embodiment is advantageous, for example, if methyl methacrylate is removed together with methanol from the reaction mixture. The weight ratio of the amount of methyl methacrylate added during the transesterification to the amount of methanol/methyl methacrylate mixture separated off can preferably be in the range from 2:1 to 1:3.

In the case of batch processes, excess starting material, in particular the unreacted ester of methacrylic acid, can be separated off by distillation towards the end of the reaction. This too can be reused without further purification in the next batch.

The methanol- or ethanol-rich distillate obtained at the beginning of the reaction can likewise be recycled, for example by introduction into a coupled plant for preparing the methacrylate ester to be transesterified.

A suitable plant for carrying out the present transesterification can comprise, for example, a stirred tank reactor provided with agitator, steam heating, distillation column and condenser. Such plants are known per se and are described, for example, in Ullmanns Encyclopedia of Industrial Chemistry (6th Edition), Verlag Wiley-VCH, Weinheim 2003, Volume 10, page 647. The size of the plant depends on the amount of butanediol dimethacrylate to be prepared, with the present process being able to be carried out either on a laboratory scale or on an industrial scale. According to a particular aspect, the stirred tank reactor can accordingly have a tank volume in the range from 1 $m^3$ to 30 $m^3$, preferably from 3 $m^3$ to 20 $m^3$. The agitator of the reactor tank can, in particular, be configured in the form of an anchor stirrer, impeller, paddle stirrer or Inter-MIG stirrer.

The task of the distillation column is to ensure that a methanol- or ethanol-rich azeotrope is taken off in order to minimize the losses of starting ester which is inevitably discharged. The distillation column can have one, two or more separation stages. The number of separation stages is the number of trays in the case of a tray column or the number of theoretical plates in the case of a column containing ordered packing or random packing elements. Examples of trays in a multistage distillation column are bubblecap trays, sieve trays, tunnel trays, valve trays, slotted trays, sieve-slotted trays, sieve-bubblecap trays, nozzle trays, centrifugal trays, examples of random packing elements in a multistage distillation column are Raschig rings, Lessing rings, Pall rings, Berl saddles, Intalox saddles and examples of ordered packing in a multistage distillation column are Mellapak (Sulzer), Rombopak (Kühni), Montz-Pak (Montz). Conversion-dependent adaptation of the reflux ratio enables, for example when using methyl methacrylate, a proportion of methanol in the distillate which is above 60% to be obtained over a wide conversion range.

Suitable condensers which can be present in the plant for carrying out the present transesterification include, inter alia, plate heat exchangers and shell-and-tube heat exchangers.

After the reaction is complete, the butanediol dimethacrylate obtained frequently meets the exacting requirements indicated above, so that further purification is frequently not necessary. To increase the quality further and, in particular, to separate off the catalyst, the mixture obtained can be purified by known methods.

In an embodiment of the process of the invention, the product mixture obtained can be purified by means of filtration processes. These processes are known from the prior art (W. Gösele, Chr. Alt in Ullmann's Encyclopedia of Industrial Chemistry, (6th Edition), Verlag Wiley-VCH, Weinheim 2003, Volume 13, pages 731 and 746), which can be carried out using customary filtration aids such as bleaching earth and aluminium silicate (Perlite). For example, it is possible to use, inter alia, continuously operable filters for a washcoat filtration.

A further improvement in the quality of the product can be achieved, for example, by separating off low boilers from the filtrate obtained. Here, it is possible to use, for example, a continuous evaporator having a rotating wiper system and super-posed column. Such apparatuses are known (Ullmanns Encyclopedia of Industrial Chemistry (6th Edition), Verlag Wiley-VCH, Weinheim 2003, Volume 36, page 505). This distillation can, for example, be carried out at a pressure in the range from 5 to 60 mbar and an evaporator temperature of from 120° C. to 150° C.

The present invention is illustrated below with the aid of examples and comparative examples, without this constituting a restriction.

EXAMPLE 1

788 kg of 1,4-butanediol, 2664 kg of methyl methacrylate (MMA), 0.123 kg of hydroquinone monomethyl ether as inhibitor and a mixture of 5 kg of calcium oxide, 1 kg of lithium hydroxide and 4 kg of water as catalyst are combined in a 6 $m^3$ stirred tank reactor provided with agitator, steam heating, distillation column and condenser and the mixture is stirred while passing in air. To stabilize the column, a total of 151 kg of MMA containing 0.24 kg of hydroquinone monomethyl ether and 0.016 kg of 4-hydroxy-2,2,6,6-tetramethylpiperidin-1-oxyl in dissolved form are introduced into the column runback during the course of the reaction. The apparatus is heated to a temperature at the bottom of 96° C., with the column initially being operated under total reflux. As soon as the temperature at the top of the column drops to below 70° C., the methanol/MMA mixture is taken off at a reflux ratio of 2.5:1. The MMA stock in the reactor is supplemented by introduction of equal parts of MMA per part of methanol/MMA mixture taken off. Thus, a total of 1267 kg of MMA are introduced over a period of 5 hours. Over a period of 8 hours, the reflux ratio is adapted to the decreasing formation of methanol up to a value of 4.5:1. At a temperature at the bottom of 130° C., the reaction is complete and excess MMA is taken off under reduced pressure, with the pressure being gradually reduced to 100 mbar. When no more MMA distills off, the vacuum is broken. The contents of the tank, comprising the catalyst-containing 1,4-butanediol dimethacrylate, is admixed with 9 kg of bleaching earth and 6 kg of aluminium silicate (Perlite) as filter aid and freed of catalyst by washcoat filtration. The filtrate is fed into a continuous evaporator (area: 2 m$^2$) having a rotating wiper system at a pressure of 15 torr and a vaporizer temperature of 142° C. A total of 1800 kg of 1,4-butanediol dimethacrylate are obtained from the bottom product:
Composition (Determined by Gas Chromatography):

| | |
|---|---|
| 93.5% | of 1,4-butanediol dimethacrylate |
| 0.05% | of MMA |
| 0.1% | of 1,4-butanediol monomethacrylate |
| 2.08% | of 4-(methacryloyloxy)butyl 3'-(methoxy)isobutyrate (IUPAC: 4-(3-methoxy-2-methylpropanoyloxy)butyl 2-methylprop-2-enoate) |
| 2.6% | of 4-(methacryloyloxy)butyl 3'-(4''-(methacryloyloxy)butyl)isobutyrate (IUPAC: 4-(2-{[4-(2-methylprop-2-enoyloxy)butyl]oxy-carbonyl}propoxy)butyl 2-methylprop-2-enoate) |

EXAMPLE 2

792 kg of 1,3-butanediol, 2650 kg of methyl methacrylate (MMA), 0.125 kg of hydroquinone monomethyl ether as inhibitor and a mixture of 5 kg of calcium oxide, 1 kg of lithium hydroxide and 3 kg of water as catalyst are combined in a 6 m$^3$ stirred tank reactor provided with agitator, steam heating, distillation column and condenser and the mixture is stirred while passing in air. To stabilize the column, a total of 151 kg of MMA containing 0.24 kg of hydroquinone monomethyl ether and 0.016 kg of 4-hydroxy-2,2,6,6-tetramethylpiperidin-1-oxyl in dissolved form are introduced into the column runback during the course of the reaction. The apparatus is heated to a temperature at the bottom of 100° C., with the column initially being operated under total reflux. As soon as the temperature at the top of the column drops to below 70° C., the methanol/MMA mixture is taken off at a reflux ratio of 4:1. The MMA stock in the reactor is supplemented by introduction of equal parts of fresh MMA per part of methanol/MMA mixture taken off. Thus, a total of 1226 kg of MMA are introduced over a period of 5 hours. Over a period of 8 hours, the reflux ratio is adapted to the decreasing formation of methanol up to a value of 1.5:1. At a temperature at the bottom of 130° C., the reaction is complete and excess MMA is taken off under reduced pressure, with the pressure being gradually reduced to 100 mbar. When no more MMA distills off, the vacuum is broken. The contents of the tank, comprising the catalyst-containing 1,3-butanediol dimethacrylate, is admixed with 9 kg of bleaching earth and 6 kg of aluminium silicate (Perlite) as filter aid and freed of catalyst by washcoat filtration. The filtrate is fed into a continuous evaporator (area: 3.5 m$^2$) having a rotating wiper system at a pressure of 18 torr and a vaporizer temperature of 134° C. A total of 1810 kg of 1,3-butanediol dimethacrylate are obtained from the bottom product:
Composition (Determined by Gas Chromatography):

| | |
|---|---|
| 93.6% | of 1,3-butanediol dimethacrylate |
| 0.1% | of MMA |
| 0.66% | of 1,3-butanediol monomethacrylate |
| 1.8% | of 3-(methacryloyloxy)butyl 3'-(methoxy)isobutyrate (IUPAC: 3-(3-methoxy-2-methylpropanoyloxy)butyl 1-methylprop-2-enoate) |
| 2.9% | of 3-(methacryloyloxy)butyl 3'-(3''-(methacryloyloxy)butyl)isobutyrate (IUPAC: 1-methyl-3-(2-{[3-(2-methylprop-2-enoyloxy)butyl]oxy-carbonyl}propoxy)propyl 2-methylprop-2-enoate) |

Comparative Example 1

Example 1 above was essentially repeated, but no water was added to the catalyst mixture. This gave 1790 kg of 1,4-butanediol dimethacrylate having the following composition (determined by gas chromatography):

| | |
|---|---|
| 87.6% | of 1,4-butanediol dimethacrylate |
| 0.2% | of MMA |
| 0.05% | of 1,4-butanediol monomethacrylate |
| 6.1% | of 4-(methacryloyloxy)butyl 3'-(methoxy)isobutyrate |
| 5.1% | of 4-(methacryloyloxy)butyl 3'-(4''-(methacryloyloxy)butyl)isobutyrate |

Comparative Example 2

Example 2 above was essentially repeated, but no water was added to the catalyst mixture. This gave 1805 kg of 1,3-butanediol dimethacrylate having the following composition (determined by gas chromatography):

| | |
|---|---|
| 90.4% | of 1,3-butanediol dimethacrylate |
| 0.25% | of MMA |
| 0.7% | of 1,3-butanediol monomethacrylate |
| 3.5% | of 3-(methacryloyloxy)butyl 3'-(methoxy)isobutyrate |
| 4.6% | of 3-(methacryloyloxy)butyl 3'-(3''-(methacryloyloxy)butyl)isobutyrate |

Comparative Example 3

Preparation without Addition of Water but Using Calcium Hydroxide in Place of Calcium Oxide 788 kg of 1,4-butanediol, 2664 kg of methyl methacrylate (MMA) comprising 1155 kg of fresh MMA and 1509 kg recycled MMA from the vacuum distillation phase of Comparative Example 1, 0.123 kg of hydroquinone monomethyl ether as inhibitor and a mixture of 3.3 kg of calcium hydroxide and 0.5 kg of lithium hydroxide as catalyst are combined in a 6 m$^3$ stirred tank reactor provided with agitator, steam heating, distillation column and condenser and the mixture is stirred while passing in air. To stabilize the column, a total of 151 kg of MMA containing 0.24 kg of hydroquinone monomethyl ether and 0.016 kg of 4-hydroxy-2,2,6,6-tetramethylpiperidin-1-oxyl in dissolved form are introduced into the column runback during the course of the reaction. The apparatus is heated to a temperature at the bottom of 91° C., with the column initially being operated under total reflux. As soon as the temperature at the top of the column drops to below 70° C., the methanol/MMA mixture is taken off at a reflux ratio of 3:1. The MMA stock in the reactor is supplemented by introduction of equal parts of MMA per part of methanol/MMA mixture taken off. Thus, a total of 1267 kg of MMA are introduced over a period of 5 hours. Over a period of 8 hours, the reflux ratio is adapted to the decreasing formation of methanol up to a value of 6.5:1. At a temperature at the bottom of 130° C., the reaction is complete, the temperature at the top of the column is 101° C. and excess MMA is taken off under reduced pressure, with the pressure being gradually reduced to 100 mbar. When no more MMA distills off, the vacuum is broken. The contents of the tank, comprising the catalyst-containing 1,4-butanediol dimethacrylate, is admixed with 9 kg of bleaching earth and 6 kg of aluminium silicate (Perlite) as filter aid and freed of catalyst by washcoat filtration. The filtrate is fed into a continuous evaporator (area: 2 m$^2$) having a rotating wiper system at a pressure of 15 torr and a vaporizer temperature of 142° C.

A total of 1806 kg of 1,4-butanediol dimethacrylate are obtained from the bottom product:
Composition (Determined by Gas Chromatography):

| | |
|---|---|
| 82.2% | of 1,4-butanediol dimethacrylate |
| 0.1% | of MMA |
| 0.2% | of 1,4-butanediol monomethacrylate |
| 8.1% | of 4-(methacryloyloxy)butyl 3'-(methoxy)isobutyrate (IUPAC: 4-(3-methoxy-2-methylpropanoyloxy)butyl 2-methylprop-2-enoate) |
| 6.1% | of 4-(methacryloyloxy)butyl 3'-(4''-(methacryloyloxy)butyl)isobutyrate (IUPAC: 4-(2-{[4-(2-methylprop-2-enoyloxy)butyl]oxycarbonyl}propoxy)butyl 2-methylprop-2-enoate) |

Comparative Example 4

Preparation without Addition of Water but Using Calcium Hydroxide in Place of Calcium Oxide 792 kg of 1,3-butanediol, 2655 kg of methyl methacrylate (MMA) consisting of 1150 kg of fresh MMA and 1505 kg of recycled MMA from the vacuum distillation phase of Comparative Example 2, 0.125 kg of hydroquinone monomethyl ether as inhibitor and a mixture of 3.3 kg of calcium hydroxide and 0.5 kg of lithium hydroxide as catalyst are combined in a 6 m$^3$ stirred tank reactor provided with agitator, steam heating, distillation column and condenser and the mixture is stirred while passing in air. To stabilize the column, a total of 151 kg of MMA containing 0.24 kg of hydroquinone monomethyl ether and 0.016 kg of 4-hydroxy-2,2,6,6-tetramethylpiperidin-1-oxyl in dissolved form are introduced into the column runback during the course of the reaction. The apparatus is heated to a temperature at the bottom of 100° C., with the column initially being operated under total reflux. As soon as the temperature at the top of the column drops to below 70° C., the methanol/MMA mixture is taken off at a reflux ratio of 4:1. The MMA stock in the reactor is supplemented by introduction of equal parts of fresh MMA per part of methanol/MMA mixture taken off. Thus, a total of 1226 kg of MMA are introduced over a period of 5 hours. Over a period of 8 hours, the reflux ratio is adapted to the decreasing formation of methanol up to a value of 1.5:1. At a temperature at the bottom of 130° C., the reaction is complete, the temperature at the top of the column is 100° C. and excess MMA is taken off under reduced pressure, with the pressure being gradually reduced to 100 mbar. When no more MMA distills off, the vacuum is broken. The contents of the tank, comprising the catalyst-containing 1,3-butanediol dimethacrylate, is admixed with 9 kg of bleaching earth and 6 kg of aluminium silicate (Perlite) as filter aid and freed of catalyst by washcoat filtration.

The filtrate is fed into a continuous evaporator (area: 3.5 m$^2$) having a rotating wiper system at a pressure of 18 torr and a vaporizer temperature of 134° C.

A total of 1815 kg of 1,3-butanediol dimethacrylate are obtained from the bottom product:
Composition (Determined by Gas Chromatography):

| | |
|---|---|
| 84.2% | of 1,3-butanediol dimethacrylate |
| 0.15% | of MMA |
| 0.12% | of 1,3-butanediol monomethacrylate |
| 6.3% | of 3-(methacryloyloxy)butyl 3'-(methoxy)isobutyrate (IUPAC: 3-(3-methoxy-2-methylpropanoyloxy)-1-methylpropyl 2-methylprop-2-enoate) |
| 6.4% | of 3-(methacryloyloxy)butyl 3'-(3''-(methacryloyloxy)butyl)isobutyrate (IUPAC: 1-methyl-3-(2-{[3-(2-methylprop-2-enoyloxy)butyl]oxycarbonyl}propoxy)propyl 2-methylprop-2-enoate) |

The invention claimed is:

1. A process for preparing a butanediol dimethacrylate, comprising:
   transesterifying butanediol with an ester of methacrylic acid in the presence of a catalyst,
   wherein a combination comprising at least one lithium compound and at least one calcium compound is used as catalyst, at least one of the compounds of lithium and/or of calcium is an oxide, a hydroxide, an alkoxide having from 1 to 4 carbon atoms or a carboxylate having from 1 to 4 carbon atoms and at least part of the reaction is carried out in the presence of an effective amount of water;
   wherein the effective amount of water, based on the weight of the butanediol used, is in the range from 0.01 to 4% by weight.

2. The process according to claim 1, wherein 1,4-butanediol is used.

3. The process according to claim 1, wherein 1,3-butanediol is used.

4. The process according to claim 1, wherein water is added to the reaction mixture.

5. The process according to claim 1, wherein the amount of water, based on the weight of the butanediol used, is in the range from 0.1 to 1% by weight.

6. The process according to claim 1, wherein the ratio of the weight of water to the weight of the catalyst is in the range from 5:1 to 1:5.

7. The process according to claim 1, wherein the ratio of the weight of water to the weight of the lithium compound is in the range from 20:1 to 1:1.

8. The process according to claim 1, wherein the ratio of the weight of water to the weight of the calcium compound is in the range from 10:1 to 1:2.

9. The process according to claim 1, wherein lithium hydroxide, lithium oxide, lithium methoxide and/or lithium ethoxide is used as the lithium compound.

10. The process according to claim 1, wherein calcium oxide, calcium hydroxide, calcium methoxide and/or calcium ethoxide is used as the calcium compound.

11. The process according to claim 1, wherein a mixture comprising lithium hydroxide and calcium oxide is used as the catalyst.

12. The process according to claim 1, wherein a mixture comprising lithium hydroxide and calcium hydroxide is used as the catalyst.

13. The process according to claim 1, wherein the ratio of the weight of the lithium compound to the weight of the calcium compound is in the range from 20:1 to 1:20.

14. The process according to claim 13, wherein the ratio of the weight of the lithium compound to the weight of the calcium compound is in the range from 1:1 to 1:10.

15. The process according to claim 1, wherein the reaction time is in the range from 2 to 20 hours.

16. The process according to claim 15, wherein the reaction time is in the range from 6 to 12 hours.

17. The process according to claim 1, wherein methyl methacrylate is used as the ester of methacrylic acid.

18. The process according to claim 1, wherein ethyl methacrylate is used as the ester of methacrylic acid.

19. The process according to claim 1, wherein the weight ratio of butanediol to the ester of methacrylic acid is in the range from 1:2 to 1:20.

20. The process according to claim 19, wherein the weight ratio of butanediol to the ester of methacrylic acid is in the range from 1:3 to 1:10.

21. The process according to claim 1, wherein the reaction is carried out at a pressure in the range from 500 to 1300 mbar.

22. The process according to claim 1, wherein the reaction is carried out at a temperature in the range from 90° C. to 130° C.

23. The process according to claim 1, wherein the temperature at which the reaction occurs is increased during the course of the reaction.

24. The process according to claim 22, wherein the temperature at the beginning of the reaction is in the range from 90° C. to 110° C. and that towards the end of the reaction is in the range from 115° C. to 130° C.

25. The process according to claim 1, wherein the reaction is carried out in the presence of a polymerization inhibitor.

26. The process according to claim 25, wherein a phenol is used as the polymerization inhibitor.

27. The process according to claim 1, wherein the reaction is carried out with the introduction of oxygen.

28. The process according to claim 1, wherein the alcohol liberated from the ester of methacrylic acid used is separated off by distillation.

29. The process according to claim 28, wherein methanol or ethanol is separated off.

30. The process according to claim 28, wherein a mixture containing methyl methacrylate and methanol is separated off.

31. The process according to claim 28, wherein part of the mixture which has been separated off is recirculated to the following batch.

32. The process according to claim 31, wherein the proportion which is recirculated of the mixture which has been separated off is obtained at the end of the reaction.

33. The process according to claim 1, wherein methyl methacrylate is added during the transesterification.

34. The process according to claim 33, wherein the weight ratio of the amount of methyl methacrylate added during the transesterification to the amount of methanol/methyl methacrylate mixture separated off is in the range from 2:1 to 1:3.

* * * * *